United States Patent [19]
Baudet et al.

[11] Patent Number: 5,304,766
[45] Date of Patent: Apr. 19, 1994

[54] METHODS AND APPARATUS FOR SIMULTANEOUSLY TREATING A PLURALITY OF SAMPLES IN A MOIST MEDIUM

[75] Inventors: Jean-Jacques Baudet, Briare; Patrick Jacquault, Sevres, both of France

[73] Assignee: Prolabo, Paris, France

[21] Appl. No.: 826,536

[22] Filed: Jan. 27, 1992

[30] Foreign Application Priority Data

Jan. 25, 1991 [FR] France .................................. 91 01064
Sep. 17, 1991 [FR] France .................................. 91 11706

[51] Int. Cl.⁵ ............................................. H05B 6/64
[52] U.S. Cl. .................................. 219/687; 219/752; 219/744; 219/756; 422/64; 422/78
[58] Field of Search .................. 219/10.55 A, 10.55 R, 219/10.55 M, 10.55 F; 422/78, 82.11, 186, 64, 65, 63

[56] References Cited

U.S. PATENT DOCUMENTS

| | | | |
|---|---|---|---|
| 3,765,425 | 10/1973 | Stungis et al. | 219/10.55 A |
| 3,830,893 | 8/1974 | Steingiser | 219/10.55 A |
| 4,004,122 | 1/1977 | Hallier | 219/10.55 A |
| 4,054,850 | 10/1977 | Gerrish | 219/10.55 A |
| 4,347,216 | 8/1982 | Kawasaki et al. | 422/78 |
| 4,347,419 | 8/1982 | Jasper, Jr. | 219/10.55 A |
| 4,661,669 | 4/1987 | Matsushima et al. | 219/10.55 R |
| 4,681,740 | 7/1987 | Commarmot et al. | 422/78 |
| 4,693,867 | 9/1987 | Commarmot et al. | 422/64 |
| 4,788,970 | 10/1988 | Klaila | 219/10.55 A |
| 4,954,681 | 9/1990 | Ishikawa et al. | 219/10.55 A |
| 4,981,801 | 1/1991 | Suzuki et al. | 422/64 |
| 5,059,400 | 10/1991 | Bénézech et al. | 422/186 |

FOREIGN PATENT DOCUMENTS 0156742 10/1985 European Pat. Off. .
2081442 2/1982 United Kingdom .

Primary Examiner—Bruce A. Reynolds
Assistant Examiner—Tu Hoang
Attorney, Agent, or Firm—Burns, Doane, Swecker & Mathis

[57] ABSTRACT

A plurality of samples in a moist medium are treated simultaneously in a microwave cavity. The samples are conducted into the cavity through apertures formed in an upper wall of the cavity. Each aperture is surrounded by a chimney configured to create a barrier opposing the propagation of microwaves from the cavity. The samples are introduced into receptacles which extend through the chimneys. Each receptacle can be supported on the chimney a lower end of the receptacle disposed within the cavity. Alternatively, the receptacles can be in the form of continuous tubes extending through upper and lower walls of the cavity in order to convey continuous flows of the sample.

30 Claims, 8 Drawing Sheets

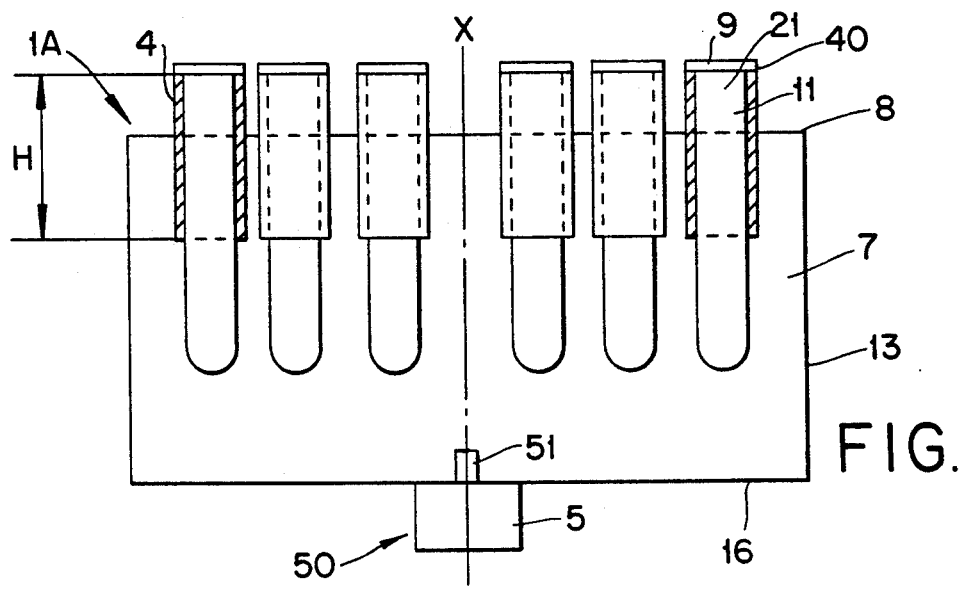
FIG. 4
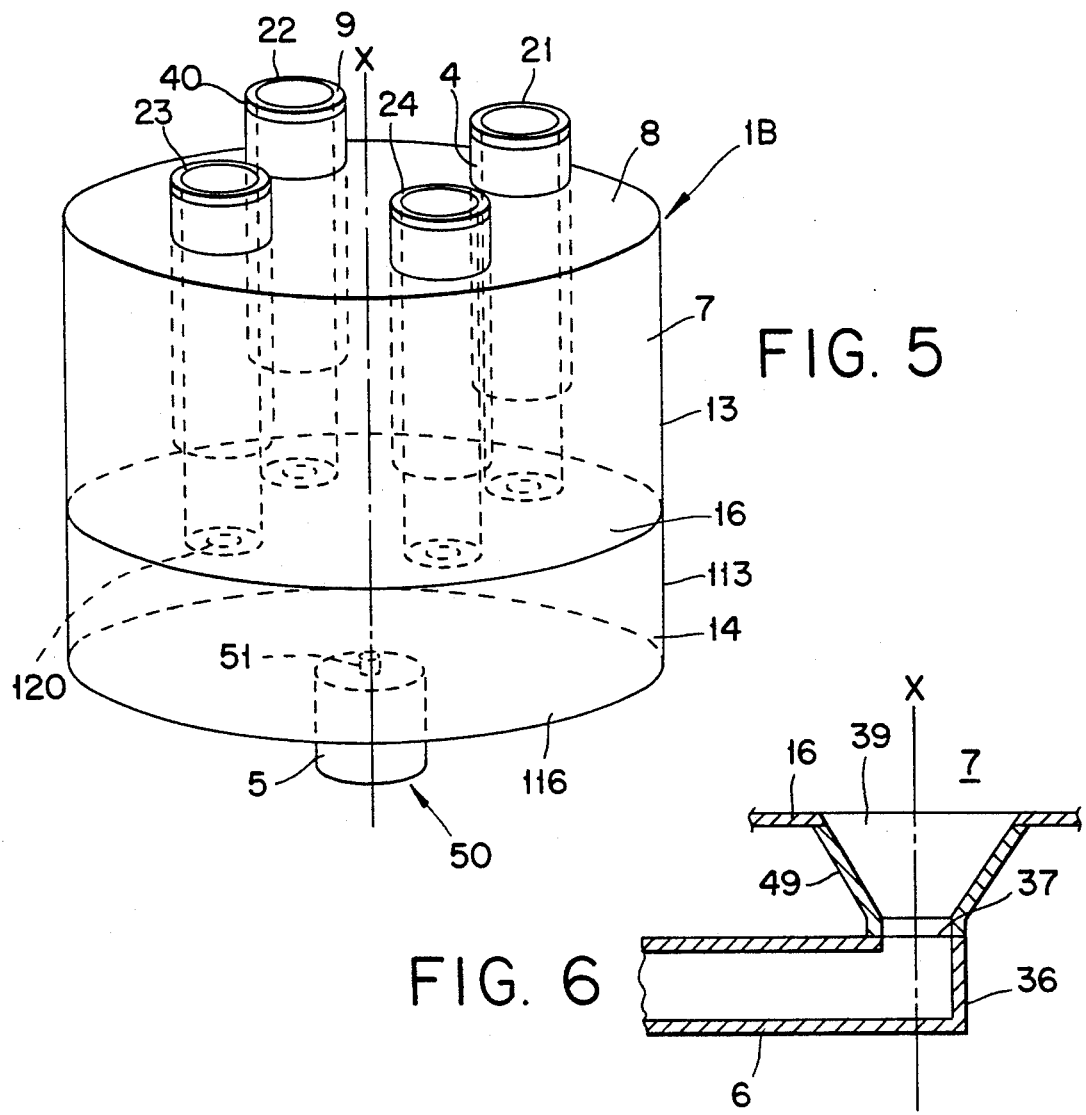
FIG. 5
FIG. 6

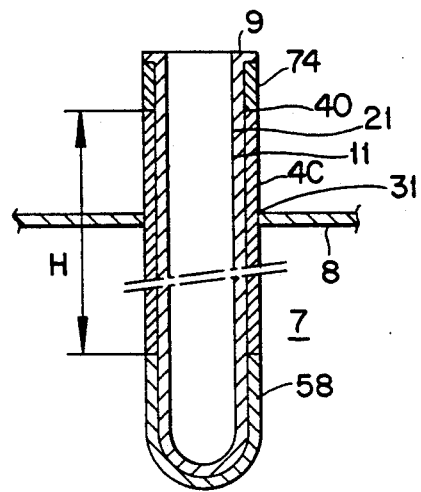
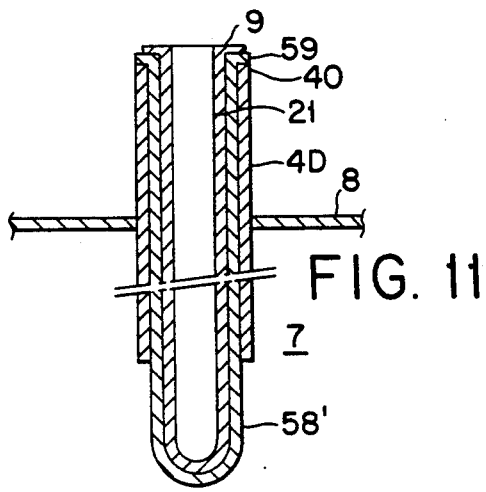
FIG. 10
FIG. 11
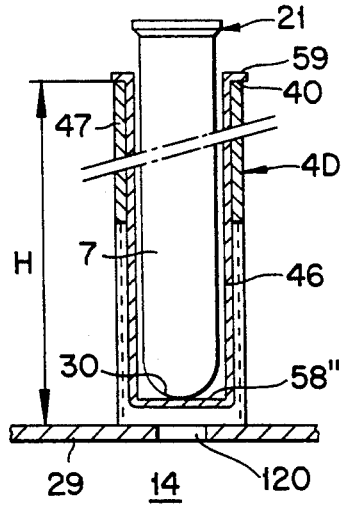
FIG. 12
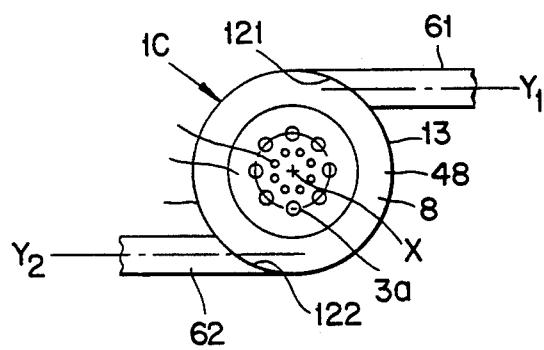
FIG. 13
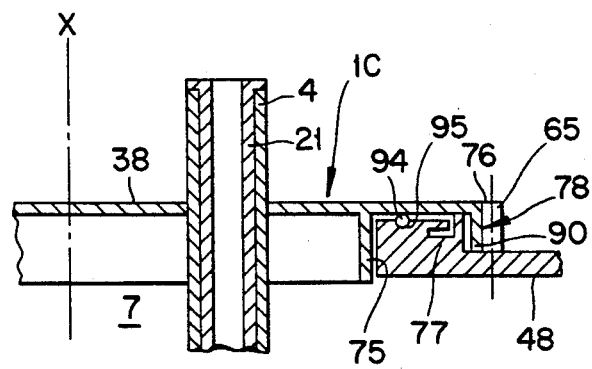
FIG. 14

METHODS AND APPARATUS FOR SIMULTANEOUSLY TREATING A PLURALITY OF SAMPLES IN A MOIST MEDIUM

BACKGROUND OF THE INVENTION

The present invention relates to an apparatus for carrying out a treatment simultaneously on a plurality of samples in a moist medium, the apparatus employing heating of the samples by microwaves. Also the invention relates to a method of utilization of the apparatus for carrying out chemical reactions on samples which may be a mineral, organic or organometallic compound, or a mixture of compounds.

There has already been described, especially in European Patent No. 156 742, an apparatus and method intended for carrying out a chemical reaction, in a moist medium, on a series of samples, the samples being prepared in advance and introduced in flasks placed into the housings of a carousel, the flasks being then brought successively into the application cavity to receive microwaves from a microwave generator. Such an apparatus is marketed by the company PROLABO under reference MICRODIGEST 300. This apparatus serves well for treating the samples individually.

In the laboratory, it is, however, sometimes necessary to be able to carry out a treatment, in a moist medium, in identical conditions of temperature and time, on a plurality of samples. Thus, the treatment should be carried out simultaneously on the plurality of samples.

It has been proposed, as described in British Patent 2 081 442, to produce an oven which heats using microwaves and which delimits an application cavity able to contain a number of receptacles suspended by their necks, whereby the entire receptacle is situated within the cavity.

Such an apparatus permits effective treatment of various samples simultaneously under the same conditions of temperature and reaction time, but does not permit easy access to the receptacles for the operator, for example, in order to introduce a supplementary reagent, or to visually monitor the progress of the reactions. In order to do that, the operator must, after switching off the microwave generator, open the front door of the oven, but that means that the receptacles are not of easy access. Moreover, in such an apparatus, the entire receptacle is heated, including its neck, and not just the part containing the sample to be treated.

One object of the invention is to provide an apparatus for carrying out a treatment, in a moist medium, on a plurality of samples.

Another object of the invention is to provide an apparatus for carrying out a treatment in a moist medium, wherein heat is applied by means of microwaves, and wherein easy access can be had to the receptacles containing the samples.

SUMMARY OF PREFERRED EMBODIMENTS OF THE INVENTION

An apparatus has now been developed according to the present invention, for treating a plurality of samples simultaneously in a moist medium, each treatment taking place in a receptacle containing one sample. The apparatus comprises means for emitting microwaves into a cavity, the cavity being a cylinder delimited by an upper wall, a lower wall and a side wall, and having an axis. The cavity has in its upper wall a plurality of apertures, each aperture having dimensions such as to permit the introduction of a receptacle into the application cavity. Each aperture is provided with a chimney of a height which is a function of the emission frequency of the microwaves and of the cross-sectional access area of the aperture, in order to form an absorption barrier opposing the propagation of the microwaves to the exterior of the application cavity.

A sample placed in a receptacle is submitted to the microwaves in order to effect rapid heating of the latter, for example, in order to carry out a chemical reaction and/or a physical operation on the sample in a moist medium.

By way of example, in such an apparatus chemical reactions can be carried out, such as mineralization, decomposition, hydrolysis etc. or physical operations such as dissolution, crystallization, evaporation, fusion etc., or a physical operation and a chemical reaction can even be combined on one and the same sample.

In the present text:

"sample", is used, for convenience, to mean the contents of the receptacle. Thus, according to the chemical reaction and/or the physical operation effected, the receptacle placed in the microwave application cavity may contain, by way of a sample, a product or a mixture of products and possibly one or more reagents;

"sample", is also used to mean a definite quantity of a product placed in a receptacle having a retention capacity, i.e., a flowing product in the form of a continuous stream in a receptacle of tubular shape;

"a plurality of samples" is used to mean that a number of samples are placed respectively in a number of receptacles, that is to say that each sample is placed with one or more reagents in a receptacle, the samples being different or identical and may or may not be associated with reagents which likewise can be different or identical;

"in a moist medium" is used to mean that the sample contains a liquid, that it is, for example, itself in the form of a liquid, or a liquid/solid mixture, or a liquid/liquid suspension, etc.

In receptacles of tubular shape, as will be described later, treatments in a moist medium can also be carried out simultaneously on a succession of samples, i.e., samples of defined volume which are successively fed into each receptacle by means of valves. Alternatively, the samples fed into each receptacle could be separated by gas bubbles (for example, air), the samples being separated by the bubbles and moving therewith in the form of a continuous stream in the tubular receptacle.

According to one embodiment, the application cavity is a cylinder whose directrix is a regular polygon.

Preferably, the application cavity is a regular cylinder whose directrix is a circle.

According to one embodiment, the means for emitting the microwaves is constituted by at least one microwave generator whose antenna is situated in the application cavity.

According to one variant, the such an apparatus comprises a microwave generator, whose antenna is situated in the application cavity along its axis.

According to another embodiment, the means for emitting microwaves into the application cavity are constituted by at least one assembly formed by a microwave generator emitting into a waveguide, the waveguide being in communication with the application cavity, and having an axis of symmetry disposed parallel to the direction of movement of the microwaves in the waveguide.

According to one embodiment, the apparatus comprises at least one waveguide which has an axis of symmetry disposed parallel to the axis of the application cavity.

According to another embodiment, the apparatus comprises a waveguide whose axis of symmetry is coincident with the axis of the application cavity.

According to yet another embodiment, the apparatus comprises at least one waveguide which has an axis of symmetry disposed orthogonally to the axis of the application cavity.

According to another embodiment, the apparatus comprises at least one waveguide whose axis of symmetry is parallel to the axis of the application cavity, and at least one waveguide whose axis of symmetry is orthogonal to the axis of the application cavity.

The apparatus for treatment in a moist medium, which is the subject of the invention, may certainly comprise, at the same time, at least one microwave emitter whose antenna is situated in the application cavity, and at least one assembly constituted by a microwave generator emitting into a waveguide.

The apparatus, according to the invention, may comprise a number of assemblies constituted by a microwave generator emitting into a waveguide.

According to one embodiment of such an apparatus, the assemblies are arranged, with respect to the application cavity of the microwaves, in such a way that the axes of symmetry of the waveguides are disposed orthogonally to the axis of the application cavity and are situated in a single plane and form secants (or are parallel) so that the apertures of the waveguides in the lateral wall of the application cavity are offset from one another circumferentially.

According to another embodiment, the assemblies are arranged, with respect to the application cavity of the microwaves, in such a way that the axes of symmetry of the waveguides are situated at different altitudes so that the apertures of the waveguides in the lateral wall of the application cavity are offset vertically from one another.

According to this embodiment, the axes of symmetry of the waveguides can be situated in a single vertical plane and/or in parallel vertical planes and/or planes forming secants.

By these arrangements the apertures of the waveguides in the lateral wall of the application cavity are never face to face.

According to yet another embodiment, for each assembly constituted by a microwave generator emitting into a waveguide, the waveguide and the application cavity have the same vertical plane of symmetry containing the axis of the application cavity.

According to another embodiment, each waveguide is arranged with respect to the application cavity in such a way that its axis is perpendicular to the axis of the application cavity.

Thus for a cylindrical application cavity whose directrix is a circle, each waveguide can be arranged radially with respect to the application cavity or can be arranged perpendicularly to a radial plane of the application cavity of the microwaves.

Preferably, the apertures in the upper wall of the application cavity are not arranged in a random way, but are arranged in at least one circle about the axis of the application cavity.

According to yet another embodiment, the application cavity of the apparatus according to the invention is such that the upper wall of the application cavity is constituted by an annular, peripheral area, forward integrally with the side wall and also by a movable central area comprising the apertures.

According to one embodiment, the movable central area is circular and is coaxial with the axis of the application cavity. The circular central area can be made to move in rotation about that axis.

According to another embodiment, the upper wall of the application cavity can be independent of the side wall and can be made to move in rotation around the axis of the application cavity.

A circular central area or an upper wall independent of the lateral wall permit, when they are made to move in rotation around the axis of the application cavity, all of the samples present in the receptacles to be subjected to the same quantity of microwaves.

The central area of the upper wall can be made to move in rotation by any known means, e.g., driven by friction by means of a turning guide wheel, or a belt; it can also be driven by means of a toothed wheel or by a chain, the central area or the upper wall being then provided with means interacting with the guide wheel or the belt or the toothed wheel or the chain.

Such a device brings a certain consistency to the distribution of the microwaves in the application cavity, even if the apparatuses according to the invention comprise, in a manner known per se, means for agitating waves, such as a wave stirrer.

The receptacles intended to contain the samples are produced from a material permeable to the microwaves, for example, glass, plastic material, etc. Their shape is not critical; their dimensions are chosen so that they can penetrate into the application cavity on the one hand, through the chimney, and on the other hand, through the aperture in the upper wall of the application cavity. Receptacles comprising an elongated neck, such as test-tubes, flasks, ampoules, usually utilized in the laboratory are well suited.

With a view to carrying out, in at least one receptacle, treatment in a moist medium on a sample flowing in a continuous stream, or on a succession of samples, the receptacle can be constituted by a tube, open at its two ends in order to permit continuous flowing of the sample stream or the succession of samples.

According to another embodiment, the receptacle can be constituted by a tube wound in a helix, whose characteristics have been determined in order to produce a sufficient dwell time of the sample in the application cavity.

For the receptacles comprising a neck, the neck of the receptacle is advantageously provided, at its upper part, with an external flange or padding strip intended to rest on the upper edge of the chimney, in order to hold the receptacle suspended. If the neck of the receptacle does not comprise an external flange or padding strip and/or if its cross-section is less than the internal cross-section of the chimney, an adaptor can be placed between the neck and the chimney.

The chimney is of cylindrical tubular shape, and of constant cross-section It rises to a height chosen as a function of the cross-sectional access area of the aperture in the upper wall of the application cavity, and of the emission frequency of the microwaves in such a way as to constitute an absorption barrier opposing the propagation of the microwaves to the exterior of the application cavity.

The chimney performs, in addition to a function of blocking propagation of the microwaves, a function of suspension of the receptacle. If the neck of the receptacle is too long with respect to the height of the chimney, an adapter can be placed between the external padding strip of the receptacle and the upper edge of the chimney. The height of the adapter will, of course, be chosen in such a way that the part of the receptacle containing the sample is located in the application cavity of the microwaves.

The chimney can be completely situated above the upper wall of the application cavity of the microwaves; it can also be, at least in part, situated inside the application cavity. However, in no case can the chimney have a height less than the height specified above for the function of forming an absorption barrier.

The chimney can be produced of any conductive material having a continuous form such as sheet metal, or having a discontinuous form such as a grid, a trellis, a woven form, or a perforated sheet.

For the apparatuses intended to receive receptacles comprising a neck, the part of each chimney situated in the application cavity is covered, by a sheath permeable to the microwaves and closed at its lower end. This prevents the sample and receptacle debris from falling into the application cavity if the receptacle breaks.

Preferably, the sheath is independent of the chimney. Thus, according to such an embodiment, in each chimney there is placed a sheath permeable to the microwaves, closed at its lower end, the sheath passing beyond the chimney into the application cavity and comprising, in its upper part, a means of being retained by upper edge of the chimney. The receptacle bears on the upper edge of the sheath, directly or by means of an adaptor.

In order to control the temperature of the chimneys, and thus the temperature of the necks of the receptacles, each chimney can comprise an annular chamber surrounding the part of the chimney situated above the upper wall of the application cavity, the said chamber being provided with fluid inlet and outlet means.

The fluid which is intended to circulate in the annular chamber is, for example, water.

In order to capture the fumes or the vapors produced by the treatment in a moist medium, the apparatus can comprise a plurality of stoppers fitted to each receptacle opening, each stopper comprising a passage linked to an exhaust and/or a means of neutralization of the gaseous products given off by the sample during the treatment.

The stoppers can be stoppers introduced into the necks of the receptacles, or can be produced of elastic material and fitted externally to the necks of the receptacles.

For receptacles constituted by a tube open at its two ends, and intended for the treatment of samples flowing continuously, the tube can comprise, upstream with respect to the direction of flow, and in its part outside the chimney, a stub duct intended for the fitting of a stopper, such as above, to the receptacle.

So that, in the receptacle, all of the volume of the sample is submitted to the microwaves in a consistent way, the apparatus can comprise means for making at least one receptacle move in rotation about its own axis oriented parallel to the axis of the application cavity.

The receptacle can be made to move in rotation about its own axis by being driven directly, for example by friction with the aid of a turning guidewheel, or by a driven belt partly surrounding the receptacle.

The receptacle can be made to move in rotation about its own axis by indirect driving, that is to say by rotating the sheath placed in the chimney or by rotating the chimney itself. The receptacle will rest on the upper edge of the sheath or on the chimney directly, or upon an adaptor. If sheath or the chimney is to be rotated, it can be rotated directly, for example by friction in the manner described above relating to the receptacle.

According to another embodiment, in order to carry out, in each receptacle, a treatment in a moist medium on a succession of samples, each receptacle can form part of a conducting circuit or loop. The loop would comprise a treatment chamber constituted by the receptacle, and a sample feed conduit located upstream of the treatment chamber (considered with reference to the direction of movement of the sample in the loop). The feed conduit can comprise an inlet conduit for at least one liquid which can be a reagent, plus a feed conduit for rinsing liquid, and, downstream from the treatment chamber, an outlet conduit for the product of the treatment, each conduit being fitted with a valve.

These conduits can be arranged in any order or position relative to one another, as long as they introduce their liquids upstream from the treatment chamber.

These conduits, each being fitted with a valve, may open out individually into the loop; they can also be in parallel and linked to a common conduit which provides the a linkage with the loop.

The apparatus can comprise a single inlet conduit for liquid; it can certainly comprise, for example for the carrying out of chemical reactions, a number of conduits for introduction of a number of reagents; these conduits can open out individually into the loop; they can also be in parallel and linked to a common conduit which provides the link with the loop.

The rinsing liquid can be, for example, water; it can also be the liquid utilized for carrying out the treatment in a moist medium.

According to one embodiment, the apparatus which is the subject of the invention can comprise, upstream from the treatment chamber, a feed conduit for an etalon, possibly fitted with a valve. This conduit can rejoin the sample feed conduit downstream from its valve.

According to a method of carrying out a treatment in a moist medium, according to the invention, a predetermined sample quantity is fed into the loop. The sampling line can thus comprise means for determining a volume or a mass of sample to be treated, especially when the latter is in solid form.

According to another embodiment, the apparatus according to the invention can be such that at least two receptacles are linked in series by a connecting branch. The connecting branch can comprise means for transferring the sample from one receptacle to the other receptacle, constituted, for example, by a pump. The connecting branch between two receptacles may possibly also comprise means for introducing a reagent into the sample transferred from one receptacle to the other.

The apparatus which is the subject of the invention may be intended to carry out treatment in a moist medium on a continuous stream of sample. The apparatus is then such that the receptacle is constituted by a tube open at its two ends and the lower wall of the cavity comprises in addition a plurality of apertures for the passage of the receptacles, each aperture being provided with a chimney of a height which is a function of the emission frequency of the microwaves and of the cross-sectional access area of the aperture, in order to form an absorption barrier to the microwaves.

An apparatus whose receptacle is constituted by a tube open at its two ends is particularly intended for the production of an apparatus of which at least two receptacles are linked in series. Thus, for example, a first receptacle will be linked by its lower part to the lower part of a second receptacle, by means of a connecting branch, and the second receptacle will be linked by its upper part to the upper part of a third receptacle by another connecting branch, and so on step by step.

The sample can circulate in the receptacles under the effect of an input pressure upstream from the first receptacle, or a suction downstream from the last receptacle.

As in the case of the chimneys surrounding the apertures situated in the upper wall, the chimneys surrounding the apertures situated in the lower wall can be at least partly situated inside the cavity of the microwaves.

In such an apparatus, each receptacle can be surrounded by a tubular sheath; the latter can, for example, (i) rest at its upper part, by a means of retention, on the upper edge of the chimney situated above the upper wall of the cavity, (ii) pass through the cavity, and (iii) enter the chimney situated below the lower wall of the cavity. Such a sheath is, obviously, produced in material permeable to the microwaves.

For an apparatus whose lower wall comprises a plurality of apertures, each aperture being provided with a chimney, the chimneys can comprise an annular chamber in their part situated below the lower wall of the application cavity, the annular chamber being provided with fluid inlet and outlet means.

According to one embodiment, the apparatus can be such that the lower wall of the application cavity is, like the upper wall, constituted by an annular, peripheral area, integral with the lateral wall, and by a central area linked to the central area of the upper wall.

According to another embodiment, the lower wall of the cavity is independent of the lateral wall and is integral with the upper wall.

In order to better steer the microwaves towards the receptacles, the cavity can, according to one embodiment of the apparatus which is the subject of the invention, comprise internal deflectors, regularly distributed and extending substantially perpendicular to the upper and lower walls of the cavity.

The deflectors are, obviously, produced in material not permeable to the microwaves.

According to one embodiment, the deflectors are substantially flat and rectangular, the axis of the cavity being situated the planes of those deflectors. According to this embodiment, the deflectors are arranged radially in the application cavity.

According to another embodiment, the deflectors are cylindrical surfaces generated about axes which are parallel to the axis of the microwave cavity, and arranged in such a way that a concave face of one deflector is opposite a convex face of the adjacent deflector. The deflectors are arranged symmetrically with respect to a plane of symmetry containing the axis of a waveguide and the cavity, the concave faces being turned towards the aperture in the lateral wall of the cavity of the corresponding waveguide.

For apparatuses, which are the subject of the invention, whose upper and lower walls are integral with the side wall, or comprising an annular area integral with the lateral wall, the deflectors can be integral with the upper and/or lower walls and/or with the annular areas.

According to one embodiment, the deflectors are integral with the side wall of the microwave cavity.

Another embodiment of the deflectors is more particularly intended for an apparatus comprising a microwave generator whose antenna is situated in the application cavity along its axis, or for an apparatus which comprises a waveguide whose axis of symmetry is coincident with the axis of the application cavity.

Such deflectors are each constituted by a cylindrical wall of generatrix parallel to the axis of the cavity, the wall substantially enveloping each receptacle and having an aperture along its part situated towards the area of the receptacle opposite the axis of the cavity, two adjacent deflectors being linked by a linking wall. The space contained between the deflectors, the linking walls and the side wall of the application cavity is filled by a material impermeable to the microwaves.

According to yet another embodiment, the apparatus, which is the subject of the invention, can be such that the means for emitting the microwaves does not emit the microwaves directly into the cavity.

The apparatus is then such that the means for emitting the microwaves emit the microwaves into a secondary cavity situated below the cavity, the wall situated between the secondary cavity and the cavity being provided with coupling windows.

Advantageously, the coupling windows are situated in a wall located between the cavity and the secondary cavity, vertically below the receptacles placed in the cavity.

According to yet another embodiment, the apparatus can be such that the means for emitting the microwaves emit the microwaves into a circular, secondary cavity having a common axis with the upper cavity. The upper wall of the lower cavity is provided with a plurality of coupling windows arranged in at least one circle, each coupling window being surrounded by a chimney situated above the upper wall of the secondary cavity. The internal space of the chimney forms an elementary microwave cavity, intended to receive the receptacle. The chimneys are of a height which is a function of the emission frequency of the microwaves into the secondary cavity and of the cross-section of the coupling windows in order to oppose the propagation of microwaves.

According to another embodiment, the apparatus comprises means for monitoring the progress of the treatments. The means for monitoring can be constituted by measurement probes placed in each receptacle within the sample, measuring, for example, the conductivity of the latter.

The apparatus for treatment in a moist medium according to the invention can be controlled manually by an operator turning on the heating by microwaves and/or possibly manoeuvering, according to a predetermined cycle, the various valves and/or the means of rotation.

Preferably, the apparatus comprises means of control, such as a microprocessor, for the turning on and the stopping of the heating by microwaves and possibly for the opening and for the closing of the various valves and/or of the means of rotation.

All the parts of the apparatus for treatment in a moist medium according to the invention, likely to be in contact with the samples, are advantageously produced in a material highly resistant to corrosion, the reagents possibly utilized being particularly aggressive, and the temperature reached in the receptacles being high. As a material, glass and polytetrafluoroethylene are generally well suited.

The apparatus for treatment in a moist medium, which is the subject of the present invention, is intended to subject samples contained in receptacles to microwaves so as to heat them rapidly, this heating having the aim of effecting a physical and/or chemical operation on the sample.

The apparatus is particularly intended to be utilized in order to carry out chemical reactions, in a moist medium, on the samples. It is particularly intended for reactions such as the acid or alkaline treatment, in a moist medium, of samples, with the aims of dissolution, hydrolysis or mineralization.

BRIEF DESCRIPTION OF THE DRAWINGS

The invention will be better understood by the description of the attached figures, which represent, by way of example, schematically, without a fixed scale, various embodiments of the apparatus which is the subject of the present invention. The apparatus will be described from now on by referring, more specifically, to an apparatus for treatment in a moist medium of samples, the treatment being a chemical reaction.

FIG. 4 is a view in vertical section through a second embodiment of an apparatus according to the invention;

FIG. 5 is a perspective view of a third embodiment of an apparatus according to the invention, comprising a secondary cavity;

FIG. 6 is a fragmentary sectional view of a variant of the manner of connection of a waveguide to a microwave cavity;

FIGS. 10 and 11 are fragmentary sectional views of two embodiments of a chimney associated with a sheath and receptacle;

FIG. 12 is a fragmentary sectional view of an embodiment of the apparatus in which each chimney constitutes an elementary microwave cavity;

FIG. 13 is a plan view of a fourth embodiment of an apparatus for treatment in a moist medium, which is the subject of the invention;

FIG. 14 is a fragmentary sectional view of the periphery of the microwave cavity of the apparatus according to FIG. 13, whose central area of the upper wall of the cavity can be made to move in rotation;

DETAILED DESCRIPTION OF PREFERRED EMBODIMENTS OF THE INVENTION

Figure 1:
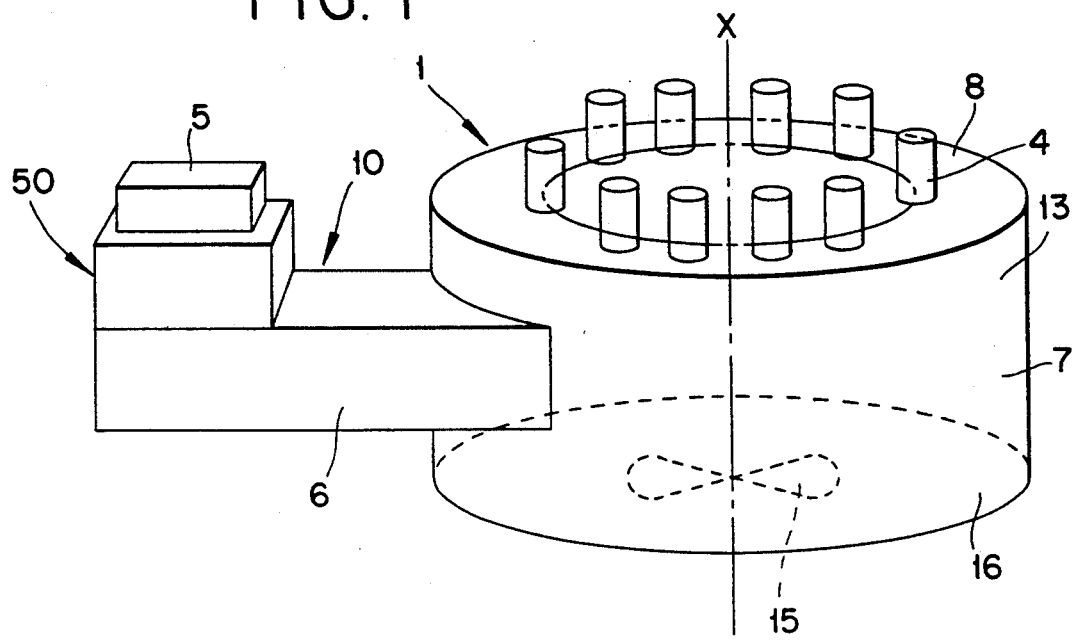
FIG. 1 is a schematic perspective view of a first embodiment of the apparatus for treating samples in a moist medium, according to the invention.

The apparatus for treatment (1) (i.e., an "apparatus for chemical reaction"), which is the subject of the invention, represented schematically in FIG. 1, is intended to carry out a chemical reaction in a moist medium, simultaneously on a plurality of samples, each reaction taking place in a receptacle (21-24) (see FIG. 2), containing the sample and at least one reagent.

The apparatus (1) comprises a mechanism (50) for emitting microwaves which includes an assembly (10) constituted by a microwave generator (5) emitting into a waveguide (6) and a microwave application cavity (7) arranged in communication with the waveguide (6).

The application cavity (7) is, according to this embodiment, a cylinder of circular cross-section and the assembly (10) is arranged in such a way that the waveguide (6) and the application cavity (7) have the same vertical plane of symmetry.

The application cavity (7) is delimited by an upper wall (8), a lower wall (16) and a lateral or side wall (13). The cavity (7) defines an axis X which is, according to this embodiment, orthogonal to the direction of movement of the microwaves in the waveguide (6).

Figure 2:
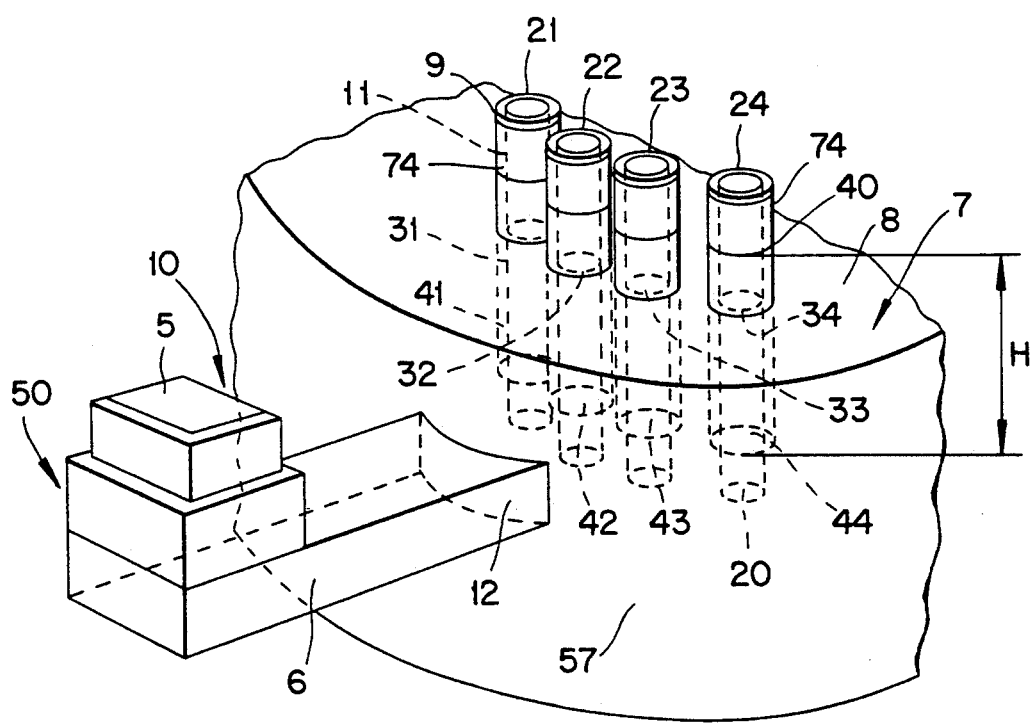
FIG. 2 is a fragmentary view of the apparatus according to FIG. 1.

The receptacles are placed in respective apertures (31-34) formed in the upper wall (8) of the cavity (7). More specifically, four receptacles (21 to 24) are placed in four apertures (31 to 34) of the upper wall (8) of the microwave cavity (7), as shown in FIG. 2.

The apparatus (1) permits the introduction of ten receptacles into the application cavity (7).

During the operation of the apparatus the receptacles (21 to 24) each containing a sample and a reagent, introduced into the application cavity (7), and are heated by the microwaves emitted by the generator (5).

The receptacles (21 to 24) are test tubes, each carrying a projection in the form of a flange (9) or padding strip at the upper part of its neck (11). Each of apertures (31 to 34) is dimensioned to permit the introduction of a receptacle into the application cavity (7).

The apertures (31 to 34) are arranged around a circle whose axis coincides with the axis X of the application cavity (7). Thus, the apertures (31 to 34) are arranged around a circle (drawn in mixed lines), symmetrically with respect to the plane of symmetry of the waveguide, which in the present case is also the plane of symmetry of the application cavity (7).

In FIG. 2 the receptacles have been represented as identical. Alternatively, an apparatus (1) can be produced which is able to receive receptacles of different dimensions; in such a case, the apertures would have dimensions adapted to the dimensions of the receptacles. However, it is preferable that the receptacles are positioned symmetrically.

Each aperture is provided with a chimney (4) having a height H, which is a function of the emission frequency of the microwaves and of the cross-sectional area of the aperture, in order to form an absorption barrier opposing the propagation of the microwaves to the exterior of the application cavity (7). In particular, chimneys (41 to 44) are shown in FIG. 4 which are of tubular cylindrical shape and constituted by sheet metal.

According to this embodiment, the chimneys (41 to 44) are situated partly in the application cavity (7). Each chimney is formed by two cylindrical sections, one being soldered above the wall (8), and the other being soldered below the upper wall (8).

Alternatively, each chimney could be a single piece. The upper wall (8) would then have a cutout in order to enable the chimneys to be put in place and soldered within the apertures (31 to 34).

The receptacles are provided with necks (11) which are long enough so that the flange (9) does not rest directly on the upper edge (40) of the chimneys (4). Adaptors in the form of cylindrical struts (74) (see FIG. 2) are placed between the flange (9) of the receptacles and the upper edge (40) of the chimneys (4) (see also FIG. 3 which depicts a strut (74) in vertical section). The height of the strut is such that the lower part of the receptacle (which carries the reagent(s) and sample) projects below the upper wall (8) and lies in the cavity (7).

The apparatus for chemical reaction (1) includes a mechanism (15) for agitating the microwaves, constituted by a wave stirrer such as a fan. The fan establishes a certain consistency to the field of microwaves in the application cavity (7).

Figure 3:
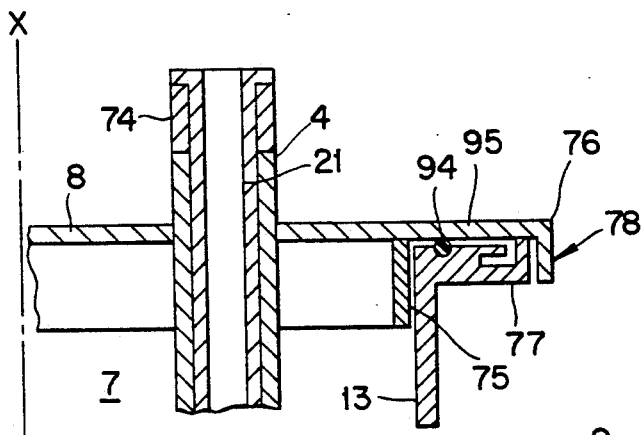
FIG. 3 is a fragmentary sectional view of the periphery of the upper wall of the cavity of an apparatus according to FIGS. 1 and 2, the upper wall being capable of rotation.

As shown in FIG. 3, the upper wall (8) is movable in rotation around the axis X of the application cavity (7) relative to the lateral wall (13) of the application cavity (7). Thus, the receptacles move along a circular path around the axis of rotation X, and thus are subjected to the same conditions of application of the microwaves.

Referring to FIG. 3, the upper wall (8) of the application cavity (7) is provided on the one hand, with a cylindrical ferrule (75) engaging in the application cavity (7) and, on the other hand, with a flange (76) which interacts with a rim (77) of the lateral wall (13) of the application cavity (7) to constitute a quarter-wave trap (78).

In order to facilitate the rotation of the upper wall (8), the latter rests on the lateral wall (13) by means of bearing balls (94) placed in a groove (95) situated in the upper part of the lateral wall (13).

Figure 15:
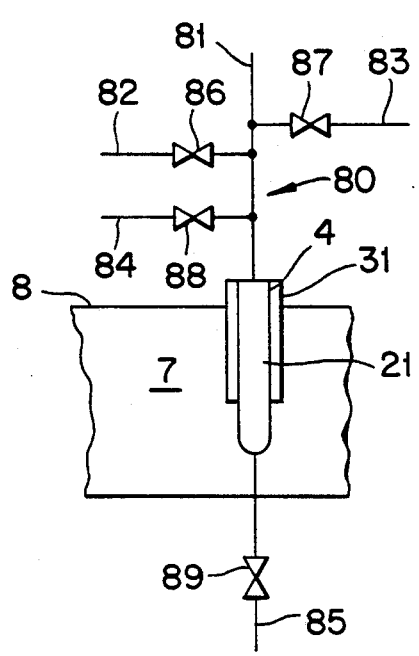
FIG. 15 is a schematic representation of an apparatus, which is the subject of the invention, permitting the carrying out in each receptacle of treatment on a succession of samples.

If the apparatus (1) is intended to carry out, in each receptacle, a chemical reaction on a succession of samples, as will be described later in connection with FIG. 15, the lower wall (16) of the application cavity (7) and the lower part of the lateral wall (13) also comprise means for constituting a quarter-wave trap, and, advantageously, the lower wall (16) is rendered integral with the upper wall (8), for example with the aid of interconnecting flanges.

A second embodiment of the apparatus for chemical reaction (1A), shown in FIG. 4, comprises, like the apparatus represented in FIGS. 1 and 2, a cylindrical application cavity (7) of circular cross section having an axis X, delimited by an upper wall (8), a lower wall (16) and a side wall (13). The mechanism (50) for emitting the microwaves into the application cavity (7) comprises a generator (5) whose antenna (51) is situated in the application cavity (7) along its axis X, the microwave generator (5) being mounted below the lower wall (16) of the application cavity (7).

The apparatus (1A) permits, like the apparatus (1) previously described, the introduction of ten receptacles into the application cavity (7) by means of apertures in the upper wall (8), the apertures (3) being arranged in a circle about axis X.

Each aperture in the upper wall (8) of the application cavity (7) is provided with a chimney (4) situated at the aperture periphery. The chimney is of cylindrical shape and has a height H, which is a function of the emission frequency of the microwaves and of the cross-sectional access area of the aperture, in order to form an absorption barrier opposing the propagation of the microwaves to the exterior of the application cavity (7). The chimneys (4) are situated partly in the application cavity (7). In this embodiment, no struts (74) are provided. Rather, the receptacles rest, by means of the flange (9), directly on the upper edge (40) of the chimneys (4).

A third embodiment of the apparatus (1B) for chemical reaction in a moist medium such as represented in FIG. 5 comprises an application cavity (7) similar to that described above, and a secondary cavity (14) situated below the application cavity (7). The secondary cavity (14) is delimited by a lower wall (116), a lateral wall (113) constituting an extension of the lateral wall (13) of the application cavity (7), and an upper wall constituted by the lower wall (16) of the application cavity (7). The secondary cavity (14) is thus cylindrical and has the same axis X as the application cavity (7).

The means (50) for emitting microwaves into the secondary cavity (14) in FIG. 5 are constituted by a generator (5) whose antenna (51) is situated in the secondary cavity (14), along the axis X of the latter, the generator (5) being placed below the lower wall (116) of the secondary cavity (14).

The wall (16) disposed between the secondary cavity (14) and the application cavity (7) is provided with coupling windows (120) situated vertically below the receptacles (2).

The apparatus (1), represented in FIG. 5, comprises four receptacles (21 to 24) in the form of a test-tube whose closed end is placed in the vicinity of the wall (16) above the coupling windows (120). Each receptacle penetrates into the application cavity (7) through an aperture fitted with a chimney (4), and rests by means of its flange (9) on the upper edge (40) of the chimney (4).

FIG. 6 is a detailed view in section of the connection of a waveguide (6) leading to an application cavity (7), the waveguide (6) conducting microwaves toward the center of the lower wall (16) of the application cavity (7) through the aperture (39) of the latter, and extending, according to the embodiment represented, perpendicular to the axis X of the application cavity (7). The waveguide (6), which can be used in any of the aforedescribed embodiments of the apparatus, has an end wall (36) and an aperture (37) located on its side wall which faces the application cavity (7) and communicating with the aperture (39) in the lower wall (16). Between the aperture (37) of the waveguide and the aperture (39) of the lower wall (16) of the application cavity (7) there is placed a connecting cone (49) diverging towards the application cavity (7). The cone is soldered on the one hand to the lower wall (16) of the application cavity (7) and, on the other hand, to the wall of the waveguide (6).

Figure 7:
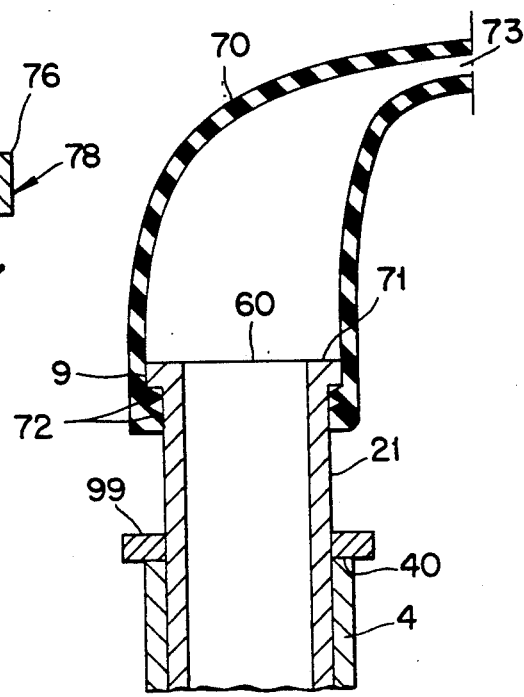
FIG. 7 is a fragmentary sectional view of a stopper associated with a chimney for capturing the gaseous products of the reaction.

In order to capture the fumes and/or the vapors produced by the chemical reaction, the receptacle, whose neck (11) is shown in FIG. 7, can comprise a stopper (70) which is shaped to fit the opening (60) of the receptacle. The stopper (70) is produced of an elastic material and is shaped to fit the receptacle (2). The stopper (70) is held by the interaction of a collar (71) situated at the upper end of the neck (11) of the receptacle and two ribs (72) situated on the inner face of the stopper (70), the two ribs (72) and the collar (71) forming a leak-tight seal.

The stopper (70) comprises a conduit (73) for removal of the fumes and/or vapors, which can be linked to means of exhaustion and/or of neutralization.

The neck (11) of the receptacle is provided externally with two lugs (99) which, like the flange (9) described previously, are intended to come to bear on the upper edge (40) of the chimney (4).

The receptacles have been described above as being open (for example in FIGS. 2 and 3) or fitted with a stopper (70) intended to capture the fumes or vapors given off (FIG. 7); they can also be provided with a stopper forming a leak-tight closure of the receptacle, the receptacle then being constituted in such a way that it can withstand an internal pressure.

Figure 8:
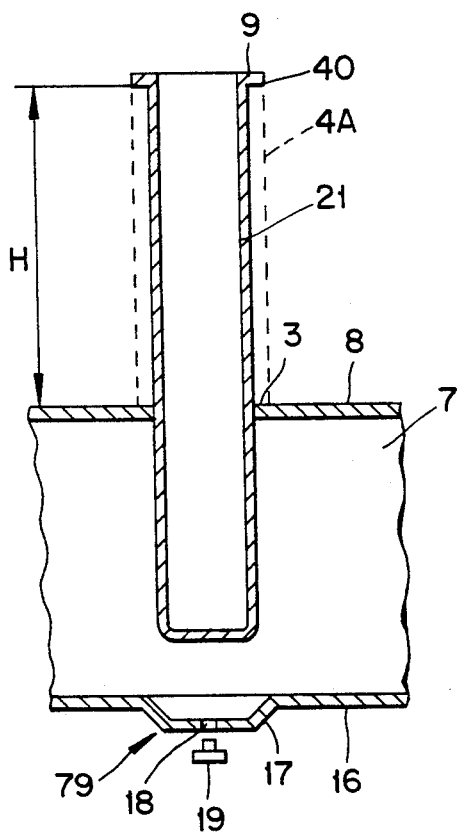
FIG. 8 is a fragmentary sectional view of an embodiment of a chimney and a receptacle.

Another embodiment of the chimney (4A) is depicted in vertical section in FIG. 8. The chimney (4A) is produced of a conductive material in a mesh-like discontinuous form, preferably in the form of a metallic trellis. The strength of the metallic trellis constituting the chimney (4A) is, determined in order to have sufficient mechanical strength, so that the chimney (4A) in addition to its function as a barrier to propagation of the microwaves, can provide the support function for the receptacle by engaging the external flange (9) at the upper edge (40) of the chimney (4).

The chimney (4A) is situated at the periphery of the aperture of the upper wall (8) of the application cavity (7). The chimney (4A) is situated entirely above the upper wall (8) of the application cavity (7) and rises to a height H chosen as a function of the cross-sectional access area of the aperture and of the emission frequency of the microwaves, so as to constitute an absorption barrier opposing the propagation of the microwaves to the exterior of the application cavity (7).

The application cavity (7) comprises, in its lower wall (16) vertically in line with the aperture (3) and immediately below the receptacle, a means of removal (79) of any product likely to be spilled in the application cavity (7) by the breaking of the receptacle. The means of removal (79) is constituted by a bowl (17) produced by swaging of the lower wall (16) or attached by soldering. The bowl (17) comprises a discharge hole (18) whose diameter can be sized so that it constitutes, by itself, an antipropagation barrier to the microwaves, or else a stopper (19) can be provided to block the hole (18).

The bowl (17) can also be removable. A person skilled in the art could certainly provide means of trapping the microwaves between a removable bowl (17) and the lower wall (16) of the application cavity (7).

Figure 9:
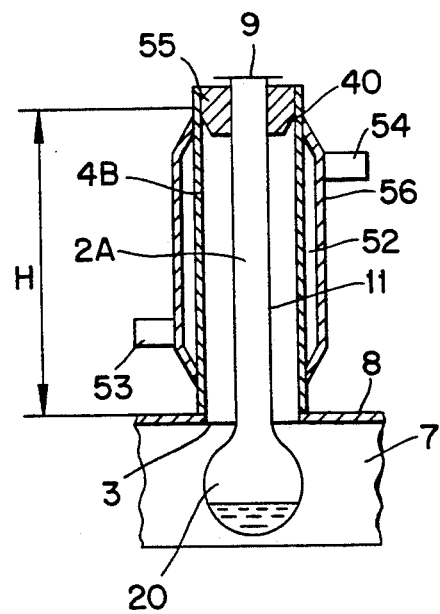
FIG. 9 is a fragmentary sectional view of another embodiment of a chimney and a receptacle.

Another embodiment of the chimney (4B) is depicted in vertical section in FIG. 9. The chimney, which is situated completely above the upper wall (8) of the application cavity (7), is produced of a conducting material in a continuous or solid construction. Here, here it is constituted by sheet metal of tubular shape and is soldered to the periphery of the aperture at the upper wall (8) of the application cavity (7). The aperture is of larger cross-section than that of the neck (11) of the receptacle (2A), so as to permit the passage of a bulging part (20) of the receptacle (2A) intended to contain the sample and the reagent or reagents.

The chimney (4B) is surrounded by a sleeve (56) delimiting an annular chamber (52). The sleeve (56) comprises two tubings (53, 54) constituting an inlet and outlet, respectively, for fluid in circulation through the chamber (52). The fluid regulates the temperature of the chimney (4B) and, thus, the temperature of the neck (11) of the receptacle as a function of the chemical reaction executed in the receptacle. By way of example, a cooling of the neck (11) of the receptacle can permit the vapors given off by the sample to condense on the neck (11) and return, under gravity, into the receptacle.

The height H of the chimney (4B) is chosen as a function of the emission frequency of the microwaves into the application cavity (7) and of the dimensions of the aperture in the upper wall (8) of the application cavity (7) in order to stop propagation of the microwaves towards the exterior of the apparatus (1).

According to the present embodiment, the external diameter of the neck (11) of the receptacle is lower than the internal diameter of the chimney (4B). In order to make it possible to hold the receptacle (2) in the apparatus (1), an adaptor (55) is placed between the upper part of the neck (11) and the upper edge (40) of the chimney (4B). The adaptor (55) is of truncated conical shape, so as to be able to engage and be held in the chimney (11). The external flange (9) of the receptacle bears on the adaptor (55).

A further embodiment of the chimney (4C) is depicted in vertical section in FIG. 10. The chimney (4C) is situated above and below the upper wall (8) of the application cavity (7). The portion of the chimney (4C) disposed within the application cavity (7) carries a sheath (58) which is permeable to the microwaves. The sheath (58) is intended to prevent the sample and debris from the receptacle from falling into the application cavity (7) if the receptacle breaks. Between the external flange (9) of the receptacle and the upper edge (40) of the chimney (4) there is interposed a strut (74).

The height H of the chimney (4C) is chosen as before, so as to constitute a barrier to the propagation of the microwaves out of the application cavity (7).

Yet another embodiment of a chimney (4D) is depicted in vertical section in FIG. 11. The chimney (4D) is enclosed by a separate sheath (58'). The sheath (58') rests, by means of flange or padding strip (59), on the upper edge (40) of the chimney (4D), and the receptacle rests, by means of its flange (9), on the flange (59) of the sheath (58').

One further embodiment of a chimney (4E) is depicted in vertical section in FIG. 12. This chimney (14E) can be used with an apparatus 1B such as disclosed in connection with FIG. 5 wherein a secondary cavity (14) is provided. The microwaves are emitted into the cylindrical, secondary cavity (14) whose upper wall (29) is provided with a plurality of the coupling windows (120) arranged in a circle about the axis X (see FIG. 5), each coupling window (120) being surrounded by a chimney (4D), situated above the upper wall (29) of the secondary cavity (14), the chimney (4D) being of cylindrical shape.

The internal space of the chimney (4) forms an elementary microwave application cavity (7) intended to receive the receptacle.

The chimney (4D), according to the embodiment represented, is constituted, in its lower part (46) by a discontinuous structure, such as a metallic mesh, and in its upper part (47) by a continuous or solid structure such as sheet metal. The chimney (4D) has a height H which is a function of the emission frequency of the microwaves into the secondary cavity (14), and of the cross-section of the coupling window (120) in order to oppose the propagation of the microwaves out of the elementary cavities (7).

In the chimney (4D) there is placed a sheath (58") which rests by means of a flange (59) on the upper edge (40) of the chimney (4D). According to this embodiment, the receptacle rests by means of its lower part (30) on the bottom of the sheath (58") directly, or a shock-absorbing material may be interposed between the lower part (30) and the sheath (58").

A fourth embodiment of the apparatus for chemical reaction (1C) according to the embodiment is depicted schematically in FIGS. 13 and 14. That apparatus (1C) comprises a cylindrical application cavity (7) and two assemblies constituted by a generator (not shown) emitting into a waveguide (61 or 62). The waveguides (61, 62) are arranged in such a way that each waveguide (61 or 62) is perpendicular to a radial plane of the application cavity (7) (i.e., a plane containing the axis X and a radius of the cavity (7)). In order to conserve a certain symmetry, the axes of symmetry (Y1, Y2) of the waveguides (61, 62) are parallel to one another. The axes (Y1, Y2) are oriented tangentially relative to the cavity (7).

The axes of symmetry (Y1, Y2) of the waveguides (61, 62) may obviously be at the same height (i.e., vertical elevation) or at different heights. Apertures (121, 122) of the waveguides (61, 62) in the lateral wall (13) of the application cavity (7) are offset from one another circumferentially and possibly also vertically.

The upper wall (8) of the application cavity (7) possesses an annular, peripheral area (48), integral with the lateral wall (13) of the application cavity (7), and a central area (38) comprising apertures (3a, 3b) which here are distributed along two concentric circles. The apertures (3a) situated furthest from the axis X of the application cavity (7) have a diameter less than that of the apertures (3b) situated around the external circle. Thus receptacles of different diameters can be placed into the application cavity (7). The apertures are fitted with chimneys (4) as defined earlier.

The central area (38) is preferably movable, and constitutes a sort of basket carrying the receptacles. The central area (38) and the peripheral area (48) are provided with means constituting a quarter-wave trap, similar to that represented in FIG. 3.

Thus, referring to FIG. 14, the central area (38) of the upper wall (8) of the application cavity (7) is provided, at its periphery, with a ferrule (75) and a flange (76) which interact with a rim (77) carried by the peripheral area (48) of the upper wall (8) so as to form a quarter-wave trap (78).

In order to facilitate rotation of the central area (38) around the axis X, the central area (38) rests on the peripheral area (48) by means of bearing balls (94) placed in a groove (95) carried by the peripheral area (48).

A toothing (65) situated on an external, lateral face (90) of the flange (76) permits, by virtue of a chain, a driving of the central area (38).

If an apparatus (1C) according to the embodiment described above is intended for carrying out, in each receptacle, a chemical reaction on a succession of samples, as disclosed below in connection with FIGS. 15–16 for example, then the lower wall of the application cavity (7) would also be constituted by a stationary peripheral area and by a rotatable central area similar to the areas (48, 38) of the upper wall. The central area of the lower wall (16) is then rendered integral with the central area (38) of the upper wall (8), for example with the aid of interconnecting flanges for common rotation.

The above-described embodiments of an apparatus for chemical reaction in a moist medium can permit carrying out in each receptacle a chemical reaction on a succession of samples. FIG. 15 is a detailed, schematic view of such an apparatus by depicting a receptacle and a chimney (4) placed in an application cavity (7).

In such an apparatus, which comprises a plurality of receptacles, each receptacle (2) forms part of a loop (80) comprising a treatment chamber, constituted by the receptacle placed in the application cavity (7). The aperture of the upper wall (8) of the application cavity (7) is provided with a chimney (4).

Referring to the direction of movement of the sample in the loop (80), the loop (80) comprises, upstream from the treatment chamber, that is to say upstream from the receptacle, a sample feed conduit (82), an inlet conduit (83) for at least one reagent, and a feed conduit (84) for rinsing liquid. Downstream from the receptacle (2), the loop (80) has an outlet conduit (85) for the discharge of the product of the treatment.

The sample feed conduit (82), the inlet conduit (83) for at least one reagent, and the feed conduit (84) for rinsing liquid are respectively fitted with valves (86, 87, 88).

The inlet conduit (83) can introduce into the loop (80) a single reagent or, successively, a number of reagents or else a mixture of at least two reagents, according to the needs of the chemical reaction.

The outlet conduit (85) for the product of the treatment is also fitted with a valve (89). The valve (89) is intended to prevent the flow of the product out of the loop (80) during the time necessary to carry out the reaction in the receptacle.

The loop (80) of the apparatus also has one conduit called a vent conduit (81), intended to make the internal space of the loop (80) open to the atmosphere. The vent conduit (81) especially permits gas generated by the chemical reaction to escape out of the loop (80).

The operation of the apparatus of FIG. 15 will be described briefly by referring to a single loop (80) comprising a single receptacle, the process described below being identical for the loop (80) of each receptacle.

The sample feed conduit (82) is linked to a source of samples, constituted, for example, by a sampling line leading from an installation. In the same way, the supply conduit (84) for rinsing liquid is 5 linked to a source of rinsing liquid.

The valves (86, 87, 88, 89) have been closed previously. The valve (86) of the sample feed conduit (82) is opened, and a predetermined quantity of sample is fed into the loop (80) (i.e., operation a), upstream from the receptacle, for example by means of a volumetric pump. The valve (86) is then reclosed.

The valve (87) of the inlet conduit (83) for a reagent is opened, and the desired quantity of reagent (i.e., operation b) is introduced into the loop (80), for example by means of a volumetric pump, then the valve (87) is reclosed.

The sample and the reagent are thus present in the receptacle. The microwave generator is then put into operation, for a predetermined time, and thus the receptacle sample and reagent located in the application cavity (7) of the microwaves are heated (i.e., operation c).

Valve (89) is then opened, and the product of the treatment is recovered through the outlet conduit (85), the product exiting from the loop (80) under the influence of gravity (i.e., operation d).

When all of the product of the treatment has been recovered, the valve (88) of the feed conduit (84) for rinsing liquid is opened, and the loop is rinsed, (i.e., operation e); the contaminated rinsing liquid exiting from the loop (80) through the conduit (85) is directed towards an effluent storage vat.

The rinsing of the loop (80) being finished, the valve (88) of the feed conduit (84) for rinsing liquid is closed, as is the valve (89) of the outlet conduit (85); the loop (80) is ready to receive a new sample fed in through the conduit (82) linked to the sampling line, and to carry out a chemical reaction in a moist medium on a new sample, repeating the operations a) to e) above.

Such an apparatus is, advantageously, controlled by a microprocessor.

The apparatus need not comprise a valve (86) on the sample feed conduit (82), nor a valve (89) on the outlet conduit (85) for the product of the treatment. Rather, the samples fed in through the conduit (82) and forming a succession of samples can be separated by gas bubbles, the samples and bubbles together forming continuous stream. In this case, the rinsing operation (e) can be carried out by the passage of the gas bubbles in the loop. In the event that such a continuous sample stream operation is desired, a structure depicted in vertical section in FIG. 16 can be used. In that structure, each receptacle (2') of the apparatus is constituted by a tube traversing the application cavity (7) and open at its two ends (68, 69); the receptacle (2') can thus be connected, on the one hand at its end (68) to an intake conduit for the sample and, possibly, for one or more reagents, and, on the other hand, connected at its end (69) to an outlet conduit for the discharge of the product of the treatment.

The receptacle (2') penetrates into the application cavity (7) through an aperture (3) 31 in the upper wall (8), and leaves again through an aperture (35) in the lower wall (16). The apertures and (35) are provided, respectively, with chimneys (4) and (45), each being of a height which is a function of the frequency of the microwaves and of the cross-sectional access area of the apertures (4, 45), in order to form absorption barriers to the microwaves.

The receptacle (2') is placed in a sheath (58''') open at its two ends. At its upper end, the sheath (58''') is provided with means of retention (59) such as a flange (9) by a means of which it rests on the upper edge (40) of the chimney (4). The sheath (58''') envelops the receptacle (2') from the top of the chimney (4) to the bottom of the chimney (45), thus enveloping all the parts thereof traversing the application cavity (7). The sheath is, of course, produced from a material permeable to microwaves.

Figure 16:
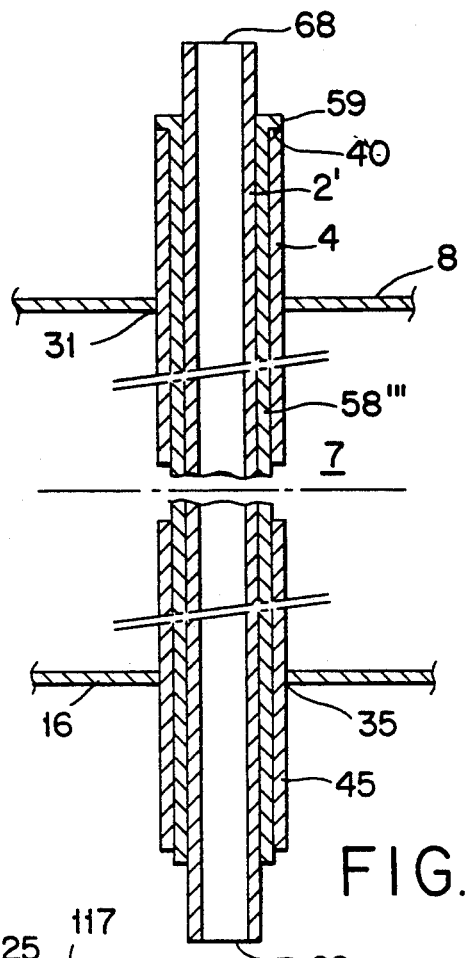
FIG. 16 is a fragmentary sectional view of a receptacle associated with two chimneys according to another embodiment of an apparatus which is the subject of the invention.
Figure 17:
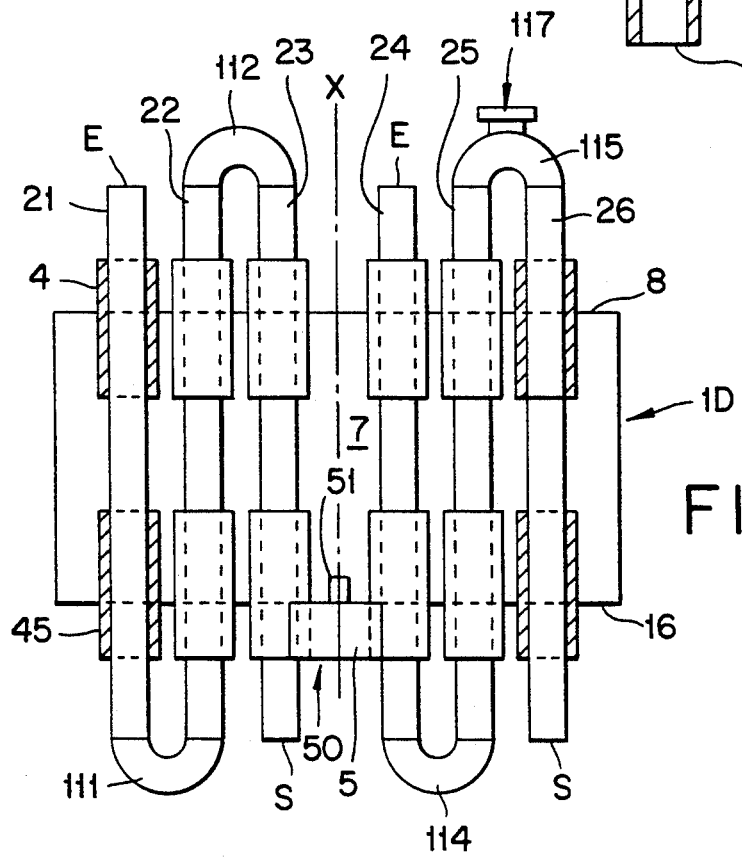
FIG. 17 is a fragmentary sectional view of a fifth embodiment of an apparatus, in which the receptacles are tubes.

A fifth embodiment of an apparatus (1D) is depicted schematically in FIG. 17. In that embodiment twelve tubular receptacles (21-26) are associated with chimneys (4, 45) in the vicinity of the upper (8) and lower (16) walls, in the same manner shown in FIG. 16.

The application cavity (7) of the microwaves is cylindrical and has an axis X, the receptacles being arranged in a circle about axis X, and the microwaves are emitted into the application cavity (7) by means (50) constituted by a generator (5) whose antenna (51) is situated in the application cavity (7) along its axis X.

The receptacles (21, 22, 23), on the one hand, and the receptacles (24, 25, 26), on the other hand, are linked in series by, respectively, connecting branches (111, 112) and (114, 115). The connecting branch (115) between the receptacles (25) and (26) comprises means (117) for introducing a reagent into the sample transferred from the receptacle (25) to the receptacle (26). The sample circulates in the series-connected receptacles under the influence of the feed pressure of the liquid from the inlets E of the receptacles (21, 24) to the outlets S of the receptacles (23, 26).

Such an apparatus can permit, like the apparatus represented in FIG. 16, the carrying out of a chemical reaction in a moist medium on a continuous flow of samples.

Figure 18:
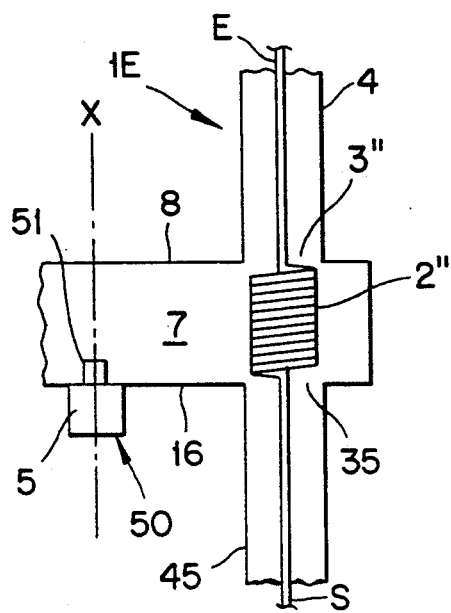
FIGS. 18 and 19 are two fragmentary sectional schematic views of sixth and seventh embodiments of an apparatus which is the subject of the invention, in which each receptacle is a tube.

A sixth embodiment of an apparatus (1E) according to the invention, is depicted in a fragmentary schematic view in FIG. 18. That apparatus comprises a number of receptacles (2''), each being constituted by a tube wound in a helix and placed in the application cavity (7). The application cavity (7) has, in its upper wall (8) and in its lower wall (16), apertures (3'', 35) for the passage of the receptacle. Associated with these apertures (3'', 35) are chimneys (4, 45) constructed in one of the ways described above.

The means (50) for emitting the microwaves into the application cavity (7) is constituted by a generator (5) whose antenna (51) is situated in the application cavity (7) along its axis X, the application cavity (7) being cylindrical, and the plurality of receptacles being in a circle about axis X.

The receptacles have their characteristics (internal diameter, diameter, pitch and number of turns of the helix) determined so that a sufficient dwell time of the sample and of the reagent or reagents in the application cavity (7) is achieved. The receptacle (2'') comprises input tubing E for the sample and the reagent or reagents, and output tubing S for the product of the treatment.

Figure 19:
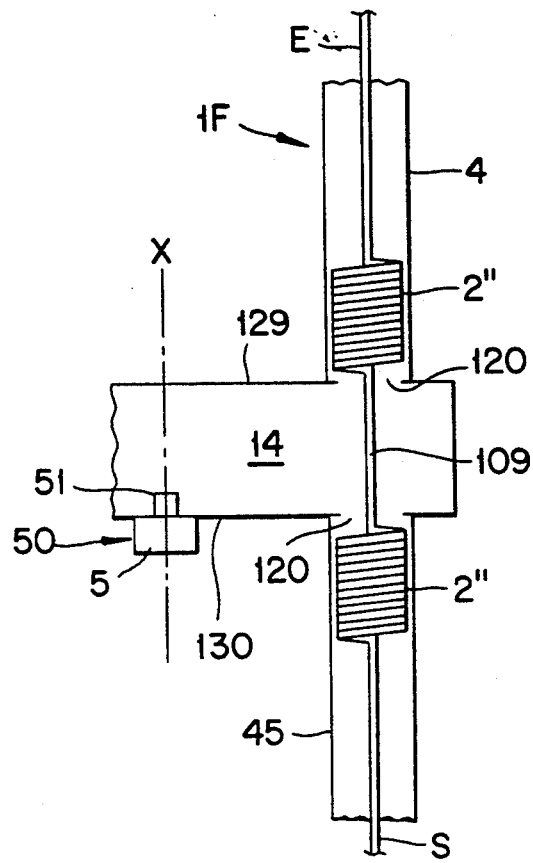

A seventh embodiment of the apparatus (1F) is shown in a partial, schematic, view in FIG. 19. The apparatus (1F) comprises a cylindrical, secondary cavity (14) having an axis X, whose upper (129) and lower (130) walls are provided with a plurality of coupling windows (120) arranged in at least one circle about axis X. Pairs of the coupling windows (120) of the upper (129) and lower (130) walls are placed in alignment one above the other. Each coupling window (120) is surrounded by a chimney (4, 45). Chimneys (4) surround the coupling windows (120) of the upper wall (129);

chimneys (45) surround the coupling windows (120) of the lower wall (130). The inner space of each chimney (4, 45) forms an elementary microwave application cavity (7) intended to receive one of the receptacles (2").

Each receptacle is constituted by a tube wound in a helix; two corresponding receptacles are linked directly in series by a linking conduit (109) passing through the secondary cavity (14).

The means (50) for emitting the microwaves into the secondary cavity (14) is constituted by an emitter (5) whose antenna (51) is situated in the secondary cavity (14) along its axis X.

The apparatuses which form the subject of the invention according to the embodiments represented in FIGS. 18 and 19 permit the carrying out of a chemical reaction on a continuous stream of samples.

The apparatuses according to the embodiments represented in FIGS. 16, 17, 18 and 19 also permit chemical reactions to be carried out on a succession of samples, samples of defined volume being fed successively into the receptacles, with the feeding between two successive samples being interrupted, or else by feeding in samples separated by gas bubbles and flowing in the form of an essentially continuous stream into the receptacles.

Figure 20:
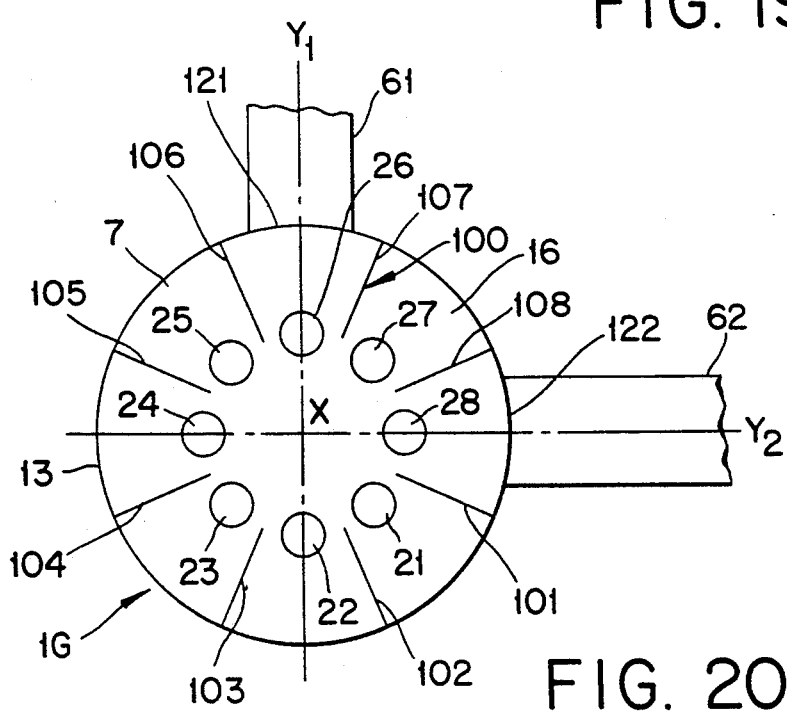
FIGS. 20, 21, and 22 depict eighth, ninth and tenth embodiments of the inventive apparatus, depicting the inside of the cavity wherein microwave deflectors are provided.
Figure 21:
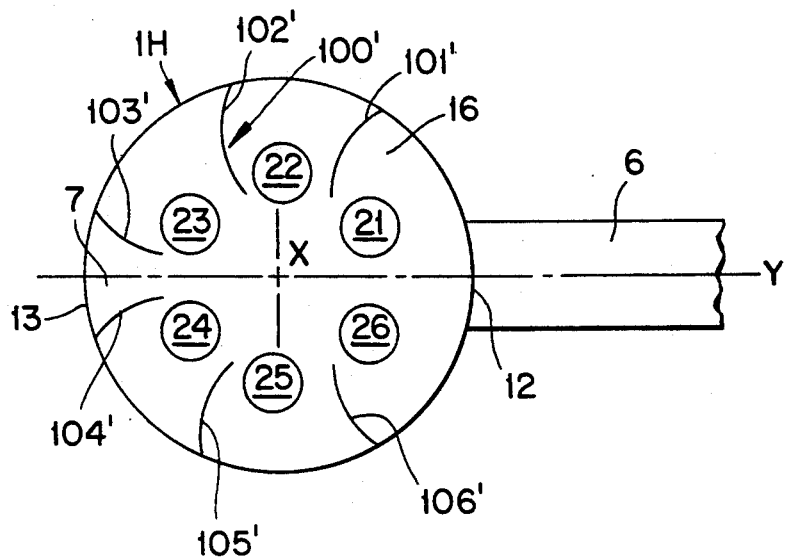
Figure 22:
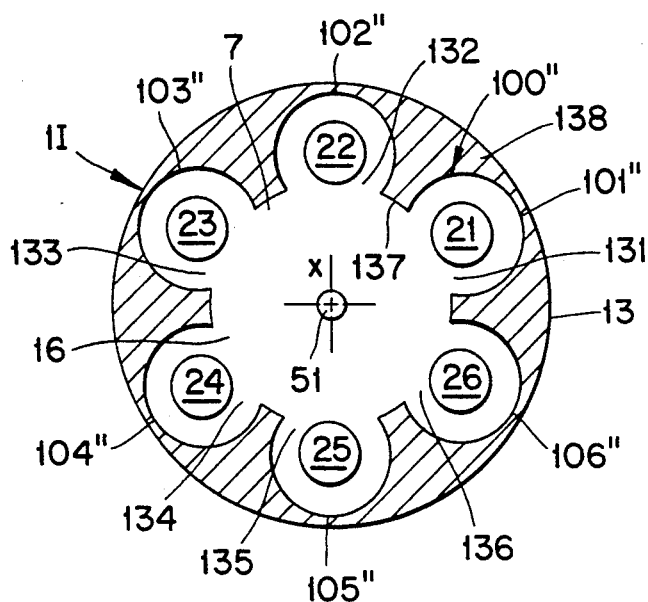

Eighth, ninth, and tenth embodiments of an apparatus (1G, 1H, 1I) are depicted in FIGS. 20, 21, 22, respectively, in horizontal section, i.e., through a plane disposed perpendicular to the axis X of the application cavity (7). Each of those embodiments includes deflectors uniformly distributed circumferentially and extending substantially perpendicular to the upper and lower walls (16) of the application cavity (7). In FIG. 20 the deflectors (100) comprise flat plates extending radially. In FIG. 21 the deflectors (100') comprise curved plates. In FIG. 22 the deflectors (100") comprise radial protrusions.

In FIGS. 20 to 22, the receptacles have been depicted schematically, the chimneys and/or the sheaths have not been depicted.

The apparatus (1G) depicted in FIG. 20 comprises a cylindrical application cavity (7), of circular cross section, and two assemblies constituted by a generator (not depicted) emitting into a waveguide (61 or 62). The waveguides (61, 62) have their axes (Y1, Y) situated in a common plane, the axes extending perpendicular to each other and to the axis X of the application cavity (7) and forming secants with the axis X. Thus, the apertures (121, 122) of the waveguides (61, 62) in the lateral wall (13) of the application cavity (7) are offset circumferentially from one another.

The apparatus (1G) comprises eight receptacles (21 to 28), distributed regularly in a circle about axis X.

The deflectors (101 to 108), formed of a material not permeable to the microwaves, are substantially flat and rectangular, the axis X of the application cavity (7) being situated at the intersection of the planes in which the deflectors (100) lie. The deflectors extend radially and are distributed uniformly among the receptacles (21 to 28).

The apparatus (1H) according to the embodiment depicted in FIG. 21 comprises a cylindrical application cavity (7) of circular directrix, and an assembly constituted by a generator (not depicted) emitting into a waveguide (6). The axis Y of the waveguide (6) is perpendicular to and forms a secant with the axis X of the application cavity (7).

The apparatus (1H) comprises six deflectors (101' to 106'), regularly distributed among the receptacles (21 to 26), symmetrically with respect to a vertical plane containing the axis Y of the waveguide (6) and the axis X of the application cavity (7). The deflectors (101' to 106') are here formed by cylindrical surfaces having axes lying parallel to the axis X of the application cavity (7). The deflectors (101' to 106') are integral with the lateral wall (13) of the application cavity (7).

The deflectors (101' to 106') are arranged symmetrically with respect to a plane of symmetry containing the axis X of the application cavity (7), and the axis Y of symmetry of the waveguides (6). On the same side of the plane of symmetry, the deflectors (101' to 103') or (104' to 106') are arranged in such a way that the concave face of one deflector (102') is opposite the convex face of the adjacent deflector (101'). The concave face is turned towards the aperture (12) of the waveguide (6) in the lateral wall (13) of the application cavity (7).

The apparatus (1I) according to the embodiment depicted in FIG. 22 comprises a cylindrical application cavity (7) of circular cross section in which the microwaves are emitted by an emitter whose antenna (51) is situated in the application cavity (7) along its axis X, the emitter being placed below the lower wall (16) of the application cavity (7).

The apparatus (1I) comprises six receptacles (21 to 26) regularly distributed in the application cavity (7) in a circle about axis X.

The deflectors (101" to 106") are each constituted by a cylindrical wall whose axis lies parallel to the axis X of the application cavity (7); the cylindrical wall of the deflectors (101' to 106') substantially envelops each receptacle (21 to 26) and has an aperture (131 to 136) along the part of its surface situated toward the area of the receptacle (21 to 26) opposite the axis X of the application cavity (7). Two adjacent deflectors such as, for example, (101', 102'), are joined by a linking wall (137). The space (138) contained between the deflectors (101' to 106'), the linking walls (137) and the lateral wall (13) of the application cavity (7) is, for preference, filled by a material impermeable to the microwaves and is preferably thermally insulating.

Figure 23:
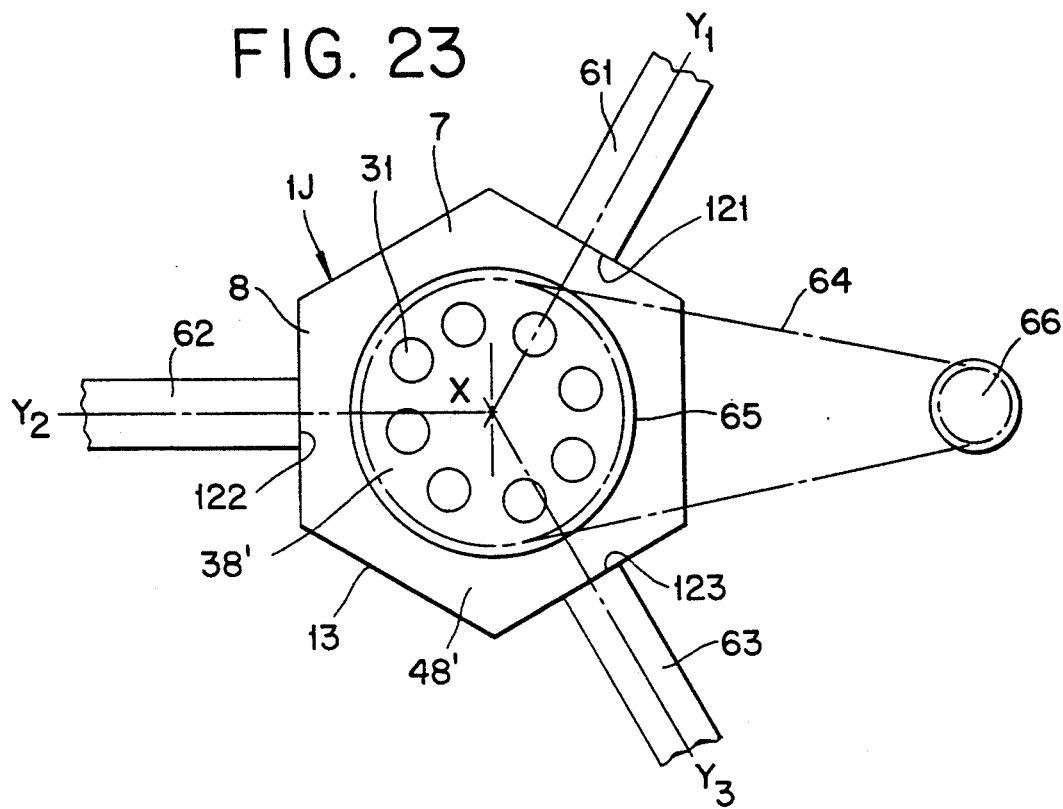
FIG. 23 is a schematic plan view of an eleventh embodiment of the apparatus comprising three assemblies constituted by a microwave generator emitting into a waveguide, whose microwave cavity is of hexagonal section and which comprises a central area made to move in rotation.

An eleventh embodiment of an apparatus (1J) for chemical reaction is depicted in top view in FIG. 23 comprises an application cavity (7) which is a cylinder whose cross section is a regular hexagon, and three assemblies constituted by a generator (not shown) emitting into a waveguide (61, 62 or 63). The waveguides (61, 62, 63) are regularly distributed; their axes (Y1, Y2, Y3) are perpendicular to the axis X of the application cavity (7), are situated in a single horizontal plane, and form a secant to the axis X. Thus, by this arrangement, the apertures (121, 122, 123) of the waveguides (61, 62, 63) in the lateral wall (13) of the application cavity (7) are circumferentially offset, no two apertures being oriented face to face.

The upper wall (8) of the application cavity (7) is also constituted by an annular, peripheral area (48'), formed integral with the lateral wall (13), and also by a central area (38') comprising the apertures (3) regularly distributed in a circle. The apertures (3) are, of course, provided with chimneys (not shown).

The central area (38') is circular and driven in rotation around the axis X of the cavity by means of a chain (64) driven in movement by a pinion (66) mounted on the shaft of a motor. The chain (64) interacts with a toothing (65) situated at the periphery of the central area (38'), such as shown in FIG. 14.

Figure 24:
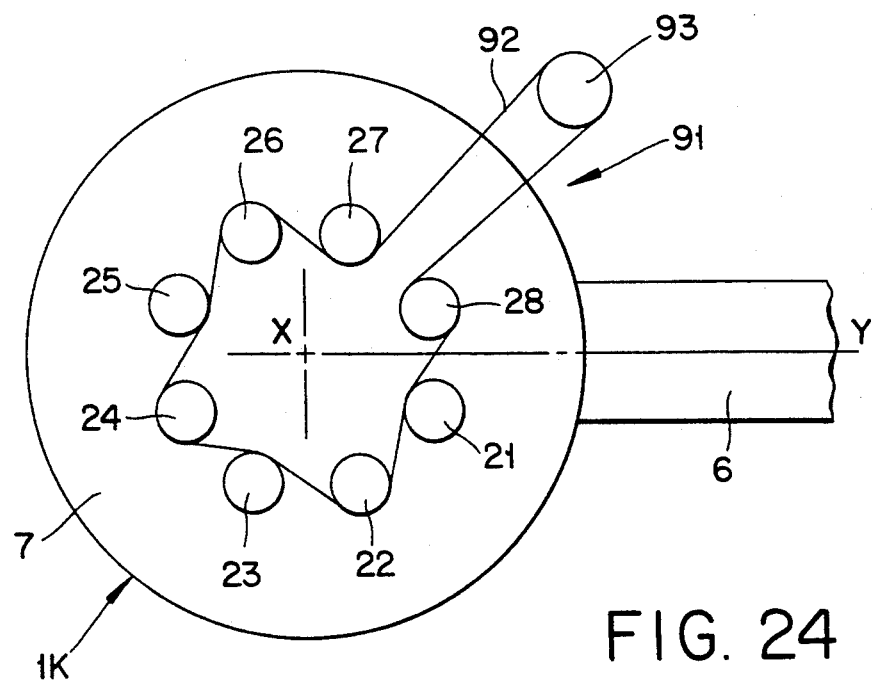
FIG. 24 is a plan view of a twelfth embodiment of an apparatus according to the invention, depicting means for making the receptacles move in rotation about their own axes.

A twelfth embodiment of an apparatus (1K) depicted in FIG. 24 includes means (91) for making at least one receptacle move in rotation about its own vertical axis disposed parallel to the axis X of the application cavity (7). The chimneys are not shown.

The apparatus (1K), schematically shown, comprises an application cavity (7), a waveguide (6) and eight receptacles (21 to 28) arranged in circle symmetrically with respect to the vertical plane of symmetry of the waveguide (6). The receptacles (21 to 28) are, according to this embodiment, made to move in rotation about their own axes by a direct drive, by means (91) constituted by a belt (92) driven by a pulley (93) mounted on the output shaft of a rotating motor.

The belt (92) partly surrounds the receptacles (21 to 28) and drives them by friction in rotation about their vertical axes. Receptacles, such as those represented in FIG. 7, are well suited for this purpose, the belt (92) surrounding their necks (11) between the lugs (99) and the padding strip (9). Instead of rotating the receptacles directly, they could be rotated indirectly, such as by having their sheaths or chimneys directly rotated. If the chimney is driven in rotation, persons skilled in the art would know to place a microwave trap around the chimney between the chimney and the upper wall of the application cavity.

Figure 25:
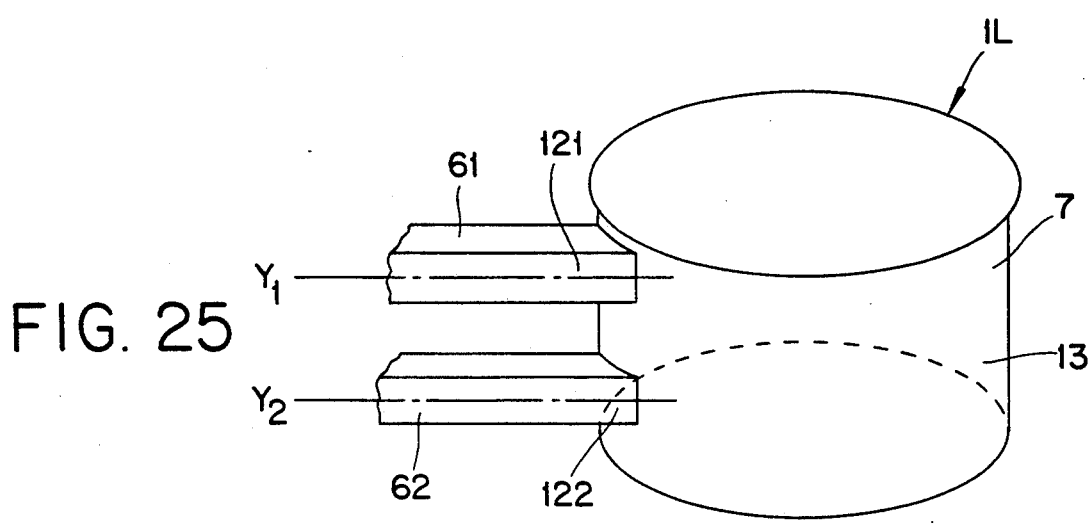
FIG. 25 is a perspective view of a thirteenth embodiment of an apparatus, according to the invention, comprising two assemblies constituted by a microwave generator emitting into a waveguide.

A thirteenth embodiment of an apparatus (1L), depicted in FIG. 25, also comprises a cylindrical application cavity (7) and two assemblies constituted by a generator (not shown) emitting into a waveguide (61 or 62). For each assembly, the waveguide (61 or 62) and the application cavity (7) have the same vertical plane of symmetry. According to the present embodiment, the axes (Y1, Y2) of symmetry of the waveguides (61, 62) are situated at different altitudes and in the same vertical plane such that the apertures (121, 122) of the waveguides (61, 62) in the lateral wall (13) of the application cavity (7) are vertically offset.

The invention is not limited to the embodiments represented and described above and, without departing from the scope of the present invention, the various variants described can be combined together.

Equally a part of the invention are other variants or embodiments within the competence of the person skilled in the art.

The apparatus for treatment in a moist medium, which forms the subject of the invention, has numerous advantages.

One of the principal advantages is that it permits carrying out treatment in a moist medium simultaneously on a number of samples under the same conditions of temperature and time period, while being easy for the operator to manipulate.

The apparatus for treatment according to the present invention, described above, is intended to carry out a chemical and/or physical treatment in a moist medium simultaneously on a plurality of samples, each treatment taking place in a receptacle containing one sample and, possibly, at least one reagent.

The apparatus according to the invention can be utilized to carry out operations of separation by heating on solid/liquid or liquid/liquid mixtures. These operations of separation, performed simultaneously on a plurality of samples, are carried out in such a way that each operation of separation takes place in a receptacle containing the solid/liquid or liquid/liquid mixture. Thus, by employing an apparatus according to the invention, the dry extract of a solid/liquid mixture, for example, can be obtained.

The apparatus according to the present invention is also intended to carry out very diverse chemical reactions. It is particularly intended to carry out chemical reactions such as the acidic or alkaline treatment, in a moist medium, of samples, with the aims of dissolution, hydrolysis or mineralization.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. Apparatus for treating a plurality of samples simultaneously in a moist medium, comprising:
   a housing having a side wall, an upper wall, and a lower wall defining a cylindrical cavity having a vertical longitudinal axis, said upper wall including a plurality of apertures each sized to receive a receptacle in which a sample is to be introduced,
   microwave supplying means comprising a microwave generating means for generating microwaves, and a waveguide for guiding the microwaves into said cavity, said waveguide having a longitudinal axis and configured to guide the microwaves in a direction parallel to said axis, and
   a chimney extending coaxially from each of said apertures, and being of a predetermined height determined as a function of both a frequency of the microwaves and a cross-sectional area of the respective aperture, for forming an absorption barrier opposing a propagation of microwaves from said cavity, said chimney being configured to receive a respective receptacle.

2. Apparatus according to claim 1, wherein each chimney extends upwardly from its respective aperture and includes means for supporting a respective receptacle to allow a lower end thereof is situated within said cavity and an upper end thereof is situated outside of said cavity.

3. Apparatus according to claim 1, wherein said receptacles, which constitute conduits passing completely through said upper and lower walls.

4. Apparatus according to claim 1, wherein said cavity constitutes an upper cavity, there being a lower cavity disposed below said upper cavity, said microwave generating means being arranged to introduce microwaves into said lower cavity, said lower wall having windows formed therein for admitting microwaves from said lower cavity to said upper cavity.

5. Apparatus according to claim 1, wherein each chimney extends upwardly from its respective aperture.

6. Apparatus according to claim 1, wherein said waveguide axis extending parallel to said axis of said cavity.

7. Apparatus according to claim 1, wherein said waveguide axis extending orthogonally to said axis of said cavity.

8. Apparatus according to claim 1, wherein there are two microwave generators, each communicating with respective waveguides, said waveguides communicating with said cavity at mutually spaced locations.

9. Apparatus according to claim 8, wherein said locations are circumferentially spaced.

10. Apparatus according to claim 9, wherein said locations are located in a common plane.

11. Apparatus according to claim 8, wherein said locations are spaced apart axially with reference to said axis of said cavity.

12. Apparatus according to claim 8, wherein said waveguides are oriented tangentially relative to said cavity.

13. Apparatus according to claim 8, wherein said waveguides are mutually parallel.

14. Apparatus according to claim 1, wherein said apertures are arranged in a circle about said vertical longitudinal axis of said cylindrical cavity.

15. Apparatus according to claim 1, wherein said upper wall includes an outer stationary portion, and a central portion which is movable relative to said outer portion, said apertures disposed in said central portion.

16. Apparatus according to claim 15, wherein said central portion is rotatable about said vertical longitudinal axis relative to said outer portion.

17. Apparatus according to claim 1, wherein said upper wall is rotatable about said vertical longitudinal axis relative to said side wall.

18. Apparatus according to claim 1, further including means for rotating at least one receptacle about its own vertical axis extending parallel to said vertical longitudinal axis of said cavity.

19. Apparatus according to claim 1, further including a conducting loop for each receptacle, each loop comprising a first inlet conduit for a sample, a second inlet conduit for rinsing liquid, and an outlet conduit for discharging liquid from the receptacle.

20. Apparatus according to claim 19, further including a valve in each of said inlet conduits and said outlet conduit.

21. Apparatus according to claim 1, wherein said receptacles in respective chimneys each comprising a tube open at its opposite ends, said lower wall including a plurality of lower apertures aligned with respective apertures in said upper wall whereby each receptacle extends through a respective pair of aligned apertures, and chimneys extending from respective ones of said lower apertures and each being of a predetermined height determined as a function of both the frequency of the microwaves and the cross-sectional area of a respective lower aperture, for forming an absorption barrier opposing the propagation of microwaves from said cavity.

22. Apparatus according to claim 21, wherein each of said receptacle which comprises a conduit extending completely through aligned pairs of said chimneys.

23. Apparatus according to claim 22, wherein each of said receptacles includes two helical portions disposed within respective ones of said chimneys.

24. Apparatus according to claim 21, wherein said lower wall is connected fixedly to said upper wall and is movable therewith relative to said side wall.

25. Apparatus according to claim 21, wherein each of said upper and lower walls includes an outer stationary portion and a control portion movable relative to said outer portion, said central portions being interconnected for common rotation, said apertures being disposed in said central portions.

26. Apparatus according to claim 1 including a plurality of deflectors disposed in said cavity, said deflectors being circumferentially spaced and extending substantially vertically.

27. Apparatus according to claim 26, wherein each of said deflectors including opposite concave and convex surfaces, a concave surface of each deflector facing a convex surface of a circumferentially successive deflector.

28. Apparatus according to claim 26, wherein each of said deflectors comprises a segment of a cylindrical surface whose axis coincides with an axis of a respective aperture.

29. Apparatus according to claim 1, wherein each of said receptacle, which constitutes conduits for conducting flows of said sample into and from said cavity.

30. Apparatus according to claim 29, wherein each of said receptacles includes an inlet and an outlet, each inlet being connected to an outlet of a preceding receptacle.

* * * * *